United States Patent [19]

Frickey et al.

[11] Patent Number: 4,670,381

[45] Date of Patent: Jun. 2, 1987

[54] HETEROGENEOUS IMMUNOASSAY UTILIZING HORIZONTAL SEPARATION IN AN ANALYTICAL ELEMENT

[75] Inventors: Paul H. Frickey; Karl J. Sanford, both of Rochester; Glen M. Dappen, Webster; Allen L. Thunberg, Pittsford; Michael W. Sundberg, Penfield; Susan J. Danielson, Rochester, all of N.Y.

[73] Assignee: Eastman Kodak Company, Rochester, N.Y.

[21] Appl. No.: 757,111

[22] Filed: Jul. 19, 1985

[51] Int. Cl.[4] .................. G01N 33/50; G01N 33/545; G01N 33/558

[52] U.S. Cl. ..................................... 435/007; 422/56; 435/21; 435/25; 435/28; 436/170; 436/501; 436/514; 436/518; 436/531; 436/810; 436/816

[58] Field of Search .............. 436/518, 523, 531, 810, 436/815, 527, 530, 535, 169, 170, 501, 514, 816; 422/56, 57, 60; 435/7, 21, 25, 28, 805

[56] References Cited

U.S. PATENT DOCUMENTS

| | | | |
|---|---|---|---|
| 2,862,796 | 12/1958 | Gomberg | 23/230 |
| 3,641,235 | 2/1972 | Weiss | 424/8 |
| 4,059,405 | 11/1977 | Sodickson et al. | 23/230 R |
| 4,094,647 | 6/1978 | Deutsch et al. | 23/253 |
| 4,258,001 | 3/1981 | Pierce et al. | 422/56 |
| 4,363,874 | 12/1982 | Greenquish | 435/7 |
| 4,366,241 | 12/1982 | Tom et al. | 422/56 |
| 4,430,436 | 2/1984 | Koyama et al. | 436/531 |

FOREIGN PATENT DOCUMENTS

| | | | |
|---|---|---|---|
| 51183 | 12/1982 | European Pat. Off. . | |
| 66648 | 12/1982 | European Pat. Off. . | |
| 0120602 | 10/1984 | European Pat. Off. | 435/7 |
| WO82/2601 | 8/1982 | PCT Int'l Appl. . | |

OTHER PUBLICATIONS

Geigel et al., *Clin. Chem,* 28(9), pp. 1894–1898 (1982).

*Primary Examiner*—Sidney Marantz
*Assistant Examiner*—David A. Saunders
*Attorney, Agent, or Firm*—J. Lanny Tucker

[57] ABSTRACT

A heterogeneous, competitive binding immunoassay is conducted with a dry analytical element. The immunoassay is useful for determining a ligand (e.g. a therapeutic drug) and includes contacting a finite area of the element spreading layer with a sample of a liquid in the presence of a labeled ligand analog and an immobilized receptor. An immobilized ligand-receptor complex is formed within the finite area. Simultaneously, the uncomplexed ligand migrates horizontally away from the immobilized complex which remains in the center of the finite area. At least five seconds after the completion of the contacting, the amount of immobilized complex is measured in the center of the finite area.

18 Claims, No Drawings

HETEROGENEOUS IMMUNOASSAY UTILIZING HORIZONTAL SEPARATION IN AN ANALYTICAL ELEMENT

FIELD OF THE INVENTION

This invention relates to clinical chemistry and to a heterogeneous, competitive binding immunoassay for the determination of an immunologically reactive ligand in a liquid. This invention is particularly useful for the determination of such ligands in aqueous liquids, such as biological fluids.

BACKGROUND OF THE INVENTION

Competitive binding immunoassays, which take advantage of natural immunological reactions, have found widespread use as analytical techniques in clinical chemistry. Because of the specificity of the reactions, they are particularly advantageous in quantifying biological analytes which are present in very low concentration and cannot be adequately quantitated by chemical techniques. Such analytes (called ligands herein) include, for example, therapeutic drugs, narcotics, enzymes, hormones, proteins, etc. Several techniques have been devised for determining very low concentrations of ligands. For instance, a ligand may be labeled by various means to make it readily measurable. In competitive binding assays, a labeled ligand analog (identified as ligand analog herein) is placed in competition with unlabeled ligand for reaction with a fixed amount of the appropriate binding material (called a receptor herein). Unknown concentrations of the ligand can be determined from the measured signal of either the bound or unbound (i.e. free) ligand analog. The reaction proceeds as follows:

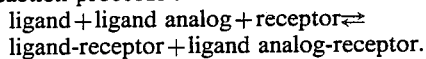

ligand-receptor + ligand analog-receptor.

Conventional labels include radioactive tags, enzymes, chromophores, fluorophores, stable free radicals, and enzyme cofactors, inhibitors and allosteric effectors.

Sensitivity is of prime importance due to the extremely low level of ligands to be measured. The first highly sensitive assays used radioactive isotopes as labels. Fluorescent or enzyme labels are currently preferred in most commercial immunoassays.

Competitive binding immunoassays can also be classified as either heterogeneous or homogeneous. Heterogeneous immunoassays require a separation of bound ligand analog from free ligand analog. This separation is necessary because the properties of bound and free analog are not significantly different. Homogeneous immunoassays do not require a separation step because the properties of the bound and free analogs are different enough so that they can be differentiated.

In PCI Publication No. 82/2601 (published Aug. 5, 1982 and assigned to American Hospital Supply Corp.), a heterogeneous immunoassay carried out on a single-layer fibrous medium is described. The described assay is carried out by immunologically precipitating and immobilizing a binding material (i.e. receptor) in a finite zone of the medium, contacting the finite zone with a sample containing the ligand and a labeled indicator, washing unreacted labeled indicator out radially from the finite zone with a stream of solvent, and measuring the amount of bound labeled indicator remaining in the finite zone.

The American Hospital immunoassay requires a separate wash step to wash the free labeled indicator horizontally away from the bound labeled indicator. It would be desirable to have an immunoassay which requires no separate step for separation of bound and free ligand analog, and is therefore simpler to use and automate.

European Patent Applications Nos. 51,183 and 66,648 (both of Fuji Photo, published May 12, 1982 and Dec. 15, 1982, respectively) describe dry multilayer, analytical elements useful for heterogeneous immunoassays. These elements comprise at least three layers, including a fibrous spreading layer, a registration layer and a radiation-blocking layer between the other layers to screen out hemoglobin or other colored whole blood components. The assay is carried out by adding a test sample to the fibrous spreading layer which has a porosity suitable to allow the applied fluid to carry unbound ligand analog to the registration layer below for reaction and spectrophotometric measurement. That is, the immunoassay carried out with this element utilizes a vertical separation of bound and free ligand analog.

U.S. Pat. No. 4,258,001 (issued Mar. 24, 1981 to Pierce et al) describes a dry multilayer analytical element containing beaded spreading layers useful for a number of assays, including immunoassays. The described element comprises a particulate porous spreading layer, a reagent layer and optionally a scavenger layer to keep hydrogen peroxide out of the spreading layer (see Col. 32). In the described assay, unbound ligand analog migrates vertically from the spreading layer into the reagent layer below after the test sample is applied to the spreading layer. This reference therefore teaches a vertical separation of bound and free ligand analog.

SUMMARY OF THE INVENTION

We have developed a simple immunoassay which does not require a separate wash step to obtain horizontal separation of bound and free ligand.

The assay of the present invention utilizes a dry analytical element which can be used in highly automated analyzers. In these elements, radial or horizontal separation of bound and free ligand occurs during the spreading of the sample. Therefore, a separate wash step is not required. The assay is simple, rapid and convenient. Minimal sample preparation is required and the assay is complete in as little as three minutes following sample contact with the element.

In one embodiment of this invention, the separation of bound and free ligand is accomplished by slowly contacting the element with the liquid sample. This ensures that the complexing of ligand and receptor occurs during sample spreading. The contacting techniques are described in more detail below.

In another embodiment of this invention, the separation of bound and free ligand is accomplished by using a beaded spreading layer with a porosity such that spreading of the liquid sample occurs slowly enough for complexation to occur during spreading. Such a spreading layer is described in more detail below.

Therefore, in one embodiment of this invention, a method for the determination of an immunologically reactive ligand in a liquid is carried out using a dry analytical element which comprises a support having thereon a porous spreading layer.

The method consists essentially of the steps of:

A. in the presence of a labeled ligand analog and a receptor for the ligand, contacting a finite area of the spreading layer with a sample of the liquid in such a manner as to form an immobilized ligand-receptor complex within the finite area, and to effect substantial horizontal separation of uncomplexed ligand from the immobilized complex, and B. at least about 5 seconds after the completion of the contacting, determining the immobilized complex within the center of the finite area.

In another embodiment of this invention, the element used has a porous spreading layer composed of a particulate structure comprising a plurality of particles having a particle size of from about 2 to about 20 $\mu$m and being bonded to each other on surface areas of adjacent particles where the adjacent particles are in closest proximity to form a coherent, three-dimensional lattice which is essentially nonswellable in an aqueous liquid. With this embodiment, the method consists essentially of the steps of:

A. in the presence of a labelled ligand analog and a receptor for the ligand, contacting a finite area of the spreading layer with a sample of the liquid to form an immobilized ligand-receptor complex within the finite area, and to effect substantial horizontal separation of uncomplexed ligand from the immobilized complex, and B. at least about 5 seconds after the completion of the contacting, determining the immobilized complex within the center of the finite area.

DETAILED DESCRIPTION OF THE INVENTION

The present invention is a specific binding assay, e.g. immunoassay, to determine an immunologically reactive species. In these assays, the species to be determined and the corresponding labeled species compete for a fixed amount of a common reactant. The species to be determined is referred to herein as a ligand, and the labeled species is referred to as a ligand analog. Compounds which specifically recognize the ligand and ligand analog and react to form complexes with them are referred to herein as receptors.

The present invention can be used to advantage to determine low concentrations of immunologically reactive ligands in a liquid, such as a biological fluid (e.g., whole blood, serum, plasma, urine, spinal fluid, suspensions of human or animal tissue, feces, saliva, lymphatic fluid and the like). The ligands can be determined at concentrations as low as about $10^{-10}$ molar, and most generally at a concentration of from about $10^{-9}$ to about $10^{-4}$ molar.

Ligands which can be so determined, either quantitatively or qualitatively, include therapeutic drugs (e.g., diphenylhydantoin, phenobarbital, theophylline, gentamicin, quinidine, propanolol, tobramycin, lidocaine, procainamide and the like), natural or synthetic steroids (e.g., cortisol, aldosterone, testosterone, progesterone, estriol, etc.), hormones (e.g., thyroid hormones, peptide hormones, insulin, etc.), proteins (e.g. albumin, IgG, IgM, etc.), antigens, antibodies, and other species which will naturally react with a receptor. This invention is particularly useful for the determination of therapeutic drugs, such as theophylline, phenobarbital or diphenylhydantoin.

The immunoassay of this invention is successfully carried out with a dry analytical element comprising a support having thereon an outermost porous spreading layer which has suitable porosity for accomodating a test sample (e.g. 1 to 100 $\mu$l), diluted or undiluted. Preferably, the spreading layer is isotropically porous, which property is created by interconnected spaces between the particles comprising the zone. By isotropically porous is meant that the spreading layer uniformly spreads the applied fluid radially throughout the layer. In the context of this disclosure and the claims, substantial horizontal separation refers to separation which is significant enough for a meaningful quantification of complexed ligand to be obtained.

In one embodiment of this invention, any spreading layer can be used in an analytical element if the liquid sample is applied to the layer in such a manner as to effect substantial horizontal separation. Particular techniques for liquid application are described below.

Useful absorbent materials for making such porous spreading layers are insoluble and maintain their structural integrity when exposed to water or biological fluids such as whole blood or serum. Useful elements can have spreading layers prepared from paper, porous particulate structures, porous polymeric films, cellulose, wood, glass fibers, woven and nonwoven fibrous fabrics (synthetic and nonsynthetic) and the like. Useful materials and procedures for making such layers are well known in the art. The porous spreading layer can be prepared from any suitable fibrous or non-fibrous material or mixtures of either or both.

Useful spreading layers can be prepared using fibrous materials, either mixed with a suitable binder material or woven into a fabric, as described in U.S. Pat. No. 4,292,272 (issued Sept. 29, 1981 to Kitajima et al). Alternatively, and preferably, the spreading layer is prepared from polymeric compositions (e.g. blush polymers) or particulate materials, e.g. beads bound together with or without binding adhesives, as described in U.S. Pat. Nos. 3,992,158 (issued Nov. 16, 1976 to Przybylowicz et al) and 4,258,001 (issued Mar. 24, 1981 to Pierce et al), the disclosures of which are incorporated herein by reference in their entirety.

Various types of particulate matter, all desirably nonswellable in and chemically inert and impermeable to the liquid components, are useful for forming a spreading layer including, for example, pigments (e.g. titanium dioxide, barium sulfate, etc.), diatomaceous earth, colloidal materials, resinous or glass beads and the like. Generally, such materials are distributed in a binder material.

Particulate materials can be treated to obtain particles that adhere to each other on surface areas of adjacent particles where those particles are in closest proximity to form a coherent, three-dimensional lattice which is essentially nonswellable in the liquid to be tested.

Examples of other useful particulate materials include the polymer particles described in U.S. Pat. No. 4,430,436 (issued Feb. 7, 1984 to Koyama et al), which particles are chemically bonded to each other through reactive groups incorporated in the particles at the points of particle contact. Other useful polymer particles are described in Japanese Patent Publication No. 57(1982)-101760 (published June 24, 1982), which particles are chemically bonded to each other at points of contact with a low molecular weight adhesive compound (e.g. reaction products of biphenols, dicarboxylic acids, or amino compounds, etc ).

Particularly useful spreading layers are those having a particulate structure formed by organo-polymeric particles and a polymeric adhesive for those particles described in U.S. Pat. No. 4,258,001 (noted above). Maintaining particulate integrity of the organo-polymeric particles in the particulate structure with the polymeric adhesive prevents the coalescence and flow of the particles into the voids, and the concentration of adhesive at those particle surface areas of the structure which are contiguous to adjacent particles insures that the adhesive does not flow into and clog the voids.

The materials used to prepare the spreading layer preferred in the practice of this invention are described in considerable detail in the Pierce et al patent. Since the details and definitions of the spreading layer are provided in that reference, the present disclosure is directed to a general description of the layer while noting preferred embodiments of this invention. The thickness of the described particulate structure can be varied depending upon the size of the organo-polymeric particles. For optimum liquid spreading, the particle coverage is generally within the range of from about 25 to about 180 g/m$^2$.

The heat-stable, organo-polymeric particles useful in the practice of this invention are generally spherical beads having a particle size in the range of from about 1 to about 200 μm in diameter. Preferably, they have a particle size within the range of from about 2 to about 50 μm in diameter.

The particles can be composed of a wide variety of organic polymers, including both natural and synthetic polymers, having the requisite properties. Preferably, however, they are composed of one or more addition polymers formed from one or more ethylenically unsaturated polymerizable monomers, such as addition homopolymers of single monomers or copolymers formed from two or more of such monomers. These polymers can be prepared by any of a variety of conventional polymerization methods (e.g. solution, emulsion, dispersion, suspension, etc.). If desired, although the invention is not so limited, the particular polymer can contain one or more reaction sites to link various interactive compositions to the particles.

Particularly useful addition polymers are those formed by polymerizing one or more of the following ethylenically unsaturated polymerizable monomers, the details of which are provided in the Pierce et al patent noted above:

(a) from 0 to 100, preferably from 0 to about 99, weight percent of one or more amino-substituent-free vinyl aromatic monomers, (b) from 0 to about 25 weight percent of one or more acrylic acid esters, (c) from 0 to 100, preferably 0 to about 75, weight percent of one or more methacrylic acid esters, (d) from 0 to about 30 weight percent of one or more ethylenically unsaturated carboxylic acids.

(e) from 0 to about 75 weight percent of one or more ethylenically unsaturated nitriles, (f) from 0 to about 20 weight percent of one or more amino-substituted vinyl aromatic monomers, including the styrene monomers described in the Pierce et al patent, (g) from 0 to about 20, preferably 0 to about 10, weight percent of one or more ethylenically unsaturated monomers containing a crosslinkable group, including those which can be crosslinked with diamines or gelatin hardeners as well as those having two or more ethylenically unsaturated polymerizable groups, (h) from 0 to about 20 weight percent of one or more tertiary aminoalkyl acrylates or methacrylates, (i) from 0 to 100, preferably 0 to about 75, weight percent of one or more polymerizable, N-heterocyclic vinyl monomers, and (j) from 0 to about 20 weight percent of one or more acrylamides or methacrylamides.

Particularly useful addition polymers include those listed in Table I of the Pierce et al patent. The numbers in the brackets represent the weight ratio of monomers in the monomer blend used to prepare the polymer. Poly(vinyltoluene-co-p-t-butylstyrene-co-methacrylic acid) [61:37:2], poly(styrene-co-n-butyl acrylate) [75:25] and polystyrene are preferred polymers. The organo-polymeric particles can contain other addenda, if desired, as known in the art.

The polymeric adhesive which is useful in this invention bonds the organo-polymeric particles to one another to provide a coherent, three-dimensional lattice in the spreading layer. The details of this adhesive are provided in the Pierce et al patent, noted above. Generally, the adhesive is composed of an organic polymer different from the specific polymer contained in the particles, although quite commonly the adhesive represents a polymer containing many repeating units which are identical or similar to some of those present in the polymer composition of the particles.

Preferably, the adhesive is composed of one or more addition polymers formed from one or more ethylenically unsaturated polymerizable monomers, such as addition copolymers formed from two or more of such monomers. The adhesive can be prepared by any of a variety of conventional polymerization methods.

Generally, the amount of adhesive contained in the particulate structure is less than about 10 percent, and preferably from about 2 to about 6 percent, and more preferably from about 3 to about 4 percent to provide optimum adhesion and liquid spreading time, based on the weight of the particles.

Particularly useful addition polymers employed as adhesives are formed by polymerizing a blend of ethylenically unsaturated polymerizable monomers selected from the blends described as follows, the details of which are provided in the Pierce et al patent noted above:

A. a blend containing from about 1 to about 35, preferably from about 10 to about 30, weight percent of one or more amino-substituent-free vinyl aromatic monomers as described above, and from about 65 to about 99, preferably from about 70 to about 90, weight percent of one or more alkyl acrylates or methacrylates, B. a blend containing from about 20 to about 95, preferably from about 50 to about 95, weight percent of one or more amino-substituent-free vinyl aromatic monomers, acrylic or methacrylic acid esters or ethylenically unsaturated polymerizable monomers containing crosslinkable groups, and from about 5 to about 80, preferably from about 5 to about 50, weight percent of one or more ethylenically unsaturated polymerizable monomers having an active hydrogen or salts thereof, C. a blend containing from about 15 to 100 weight percent of one or more ethylenically unsaturated monomers selected from the group consisting of 1-vinylimidazole, N-vinyl-2-pyrrolidone, vinylbenzyl alcohol, ethyl acrylate or an acrylamide or methacrylamide, and from 0 to about 85 weight percent of one or more ethylenically unsaturated polymerizable monomers containing crosslinkable groups, and D. a blend containing from about 60 to about 98, and preferably from about 90 to about 98, weight percent of one or more acrylic or methacrylic acid esters, and from about 2 to about 40 and preferably from about 2 to about 10, weight percent of one or more ethylenically unsaturated polymerizable monomers containing one or more anionic moieties (e.g. carboxy, sulfino, sulfo, phosphono, etc. or alkali metal or ammonium salts thereof).

Particularly useful addition polymers include those listed in Table II of the Pierce et al patent and in U.S. Pat. No. 4,283,491 (issued Aug. 11, 1981 to Dappen). The numbers in the brackets represent the weight ratio of monomers in the monomer blend used to prepare the polymer. Poly(methyl acrylate-co-2-acetoacetoxyethyl methacrylate-co-2-acrylamido-2-methylpropanesulfonic acid) [88:7:5], poly(N-vinyl-2-pyrrolidone), and poly(n-butyl acrylate-co-styrene-co-2-acrylamido-2-methylpropane sulfonic acid, sodium salt) [75:20:5] are preferred adhesive polymers.

Various methods can be employed for preparing the particulate structure with the abovedescribed particles and adhesives. Specific details of useful methods are provided in the Pierce et al patent noted above.

In one embodiment of this invention, the element spreading layer is composed of the particulate structure described above with the critical feature that the particles have a particle size in the range of from about 2 to about 20 $\mu$m, and preferably of from about 4 to about 12 $\mu$m. Use of particles of this size provides appropriate capillary action and liquid sample retention time which allows the specific binding reaction to occur and uncomplexed ligand to migrate horizontally away from complexed ligand in the spreading layer. Vertical separation (i.e. layer to layer) does not occur to a significant extent.

The spreading layer of the element useful in this invention is carried on a suitable support. Such a support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (reflection, transmission or fluorescence spectroscopy). Useful support materials include polystyrene, polyesters [e.g. poly(ethylene terephthalate)], polycarbonates, cellulose esters (e.g. cellulose acetate), etc.

Preferably, the element also comprises a reagent layer containing an indicator composition. Other optional layers, e.g. subbing layers, radiation-blocking layers, etc. can be included if desired. All layers of the element are in fluid contact with each other, meaning that fluids and reagents and uncomplexed reaction products in the fluids can pass between superposed regions of adjacent layers. During spreading however, the principal migration of the uncomplexed ligand analog is horizontal rather than vertical.

The reagent layer of the element generally contains the indicator composition comprising one or more reagents dispersed in one or more synthetic or natural binder materials, such as gelatin, or other naturally-occurring colloids, homopolymers and copolymers, such as poly(acrylamide), poly(vinyl pyrrolidone), poly(N-isopropylacrylamide), poly(acrylamide-co-N-vinyl-2-pyrrolidone) and similar copolymers.

The spreading layer of the element can contain the receptor for the ligand to be determined at the time of the assay. If the ligand is an antigen, the receptor is an antibody specific for that antigen which will react with it to form a complex. If the ligand is an antibody, the receptor is the appropriate antigen. In a preferred embodiment of this invention, the ligand is a therapeutic drug (e.g. theophylline, phenobarbital or diphenylhydantoin) and the receptor is an antibody for that drug. The receptors are generally commercially available, or they can be prepared using known starting materials and procedures. Generally, the appropriate receptors, e.g. antibodies are produced by inoculating a suitable animal with ligand to produce antibodies according to an appropriate protocol, and removing the generated antibodies from the animal. These techniques are well known in the art.

The receptor can be immobilized in the spreading layer in a suitable manner. For example, the receptor can be immobilized on a carrier material, such as glass beads, polymer beads or other particles, resins, and the like. One useful carrier material is a microorganism, such as Staphylococcus aureus. Alternatively, a beaded spreading layer can serve as the carrier material so that the receptor is immobilized therein without additional carrier material. The immobilized receptor is generally in the spreading zone in an amount of from about $10^{-6}$ to about 1 g/m$^2$.

The receptor can be added to the spreading layer in an immobilized form, or immobilized therein just prior to or during the assay when the ligand analog is applied to the layer. Preferably, the receptor is immobilized in the spreading layer during element manufacture.

The assay of this invention can be carried out using any suitable label which can be attached to the ligand to form a ligand analog. Useful labels include radioactive tags, fluorescers, enzymes, enzyme inhibitors, allosteric effectors, cofacters and other known enzyme modulators. Enzymes, such as glucose oxidase, peroxidase and alkaline phosphatase, are preferred labels.

When an enzyme label is used, the substrate for the enzyme is preferably present in the element e.g. in a reagent layer. Alternatively, the substrate can be added to the element prior to or simultaneously with the liquid sample, or after completion of the binding reaction. It is within the skill of the ordinary worker in clinical chemistry to determine a suitable substrate for a given label. The substrate can be a material which is directly acted upon by the enzyme label, or a material that is involved in a series of reactions which involve enzymatic reaction of the label. If the enzyme label is peroxidase, the substrate is hydrogen peroxide. Using glucose as an example, the substrate is generally present in the reagent layer in an amount of at least about 0.01 moles/m$^2$, and preferably from about 0.01 to about 2.5 moles/m$^2$. A worker skilled in the art would know how to adjust the amount of a particular substrate for the amount of enzyme label used in the assay.

When certain labels are used, e.g. enzymes, cofactors, fluorescent compounds or enzyme modulators, the reagent layer contains an indicator composition comprising one or more reagents which provide a detectable species as a result of reaction of the label. Preferably, the indicator composition is a colorimetric indicator composition which provides a colorimetrically detectable species as a result of enzymatic reaction of an enzyme-labeled ligand analog with a substrate. The indicator composition can be a single compound which produces a detectable dye upon enzymatic reaction, or a combination of reagents which produce the dye. For example, when glucose is used as the substrate and glucose oxidase as the enzyme label, the colorimetric indicator composition can include a color coupler and oxidizable compound which react to provide a colored dye. Alternatively, the composition can include a leuco dye and peroxidase or another suitable peroxidative compound which generate a detectable dye as a result of the formation of hydrogen peroxide produced when glucose oxidase converts glucose to gluconic acid. Useful leuco dyes are known in the art and include those, for example, described in U.S. Pat. No. 4,089,747 (issued May 16, 1978 to Bruschi) and U.S. Ser. No. 612,509, filed May 21, 1984 by Babb et al. The particular amounts of the colorimetric indicator composition and its various components are within the skill of a worker in the art.

The layers of the element can contain a variety of other desirable but optional components, including surfactants, thickeners, buffers, hardeners, antioxidants, coupler solvents, and other materials known in the art. The amounts of these components are also within the skill of a worker in the art.

The ligand analogs useful in the practice of this invention can be prepared using known starting materials and procedures, or obtained commercially. Generally, the ligand moiety of the analog is attached to the label (e.g. an enzyme moiety or fluorescer) through a covalent bond.

The immunoassay of this invention can be manual or automated. In general, the amount of a ligand in a liquid is determined by taking the element from a supply roll, chip packet or other source and physically contacting a finite area of the spreading layer with a sample of the liquid (e.g. 1 to 100 µl). The finite area which is contacted is generally no more than about 100 mm². In one embodiment described above using a beaded spreading layer having 2–20 µm particles, the technique of contacting is not critical.

In another embodiment described above, contact of the sample must be accomplished in such a manner that complexation between ligand and receptor and substantial horizontal separation of uncomplexed and complexed ligand occur during liquid introduction. This contact can be carried out by hand or with a machine using a pipette or other suitable dispensing means to dispense the test sample. The sample of liquid can be applied to the element spreading layer in a number of ways to effect horizontal separation. For example, a relatively large liquid sample (e.g. up to 100 µl can be applied slowly (e.g. over at least about 5 seconds) in a continuous manner using a pipette, capillary tube or other means. Alternatively, the sample can be applied in small portions, e.g. as a series of two or more droplets (e.g. 0.1 to 1 µl) over a period of time (e.g. over at least about 5 seconds). In this embodiment, it is critical that the sample be applied slowly enough so that both ligand-receptor complexation and horizontal separation occur during spreading.

Vertical separation does not occur to a significant extent in either embodiment of the invention. Separation is essentially complete within from about 5 to about 180 seconds after completion of sample application to the element.

If the ligand analog is not incorporated in the element during manufacture, it can be mixed with the test sample simultaneously with or prior to contact with the element.

After sample application in either embodiment, the element is exposed to any conditioning, such as incubation, heating or the like, that may be desirable to quicken or otherwise facilitate obtaining the test result. No wash step need be used in the practice of this invention.

The amount of ligand is determined by passing the element through suitable apparatus for detecting the complexed ligand analog directly or the detectable species formed as a result of enzymatic reaction of an enzyme label and a substrate. For example, the species can be detected with suitable radiometric, fluorometric or spectrophotometric apparatus using generally known procedures. In an enzymatic reaction, the resulting dye is determined by measuring the reflection or transmission density or fluorescence in the center of the finite area which was contacted with the test sample. The area which is measured is generally from about 3 to about 5 mm in diameter. Most of the complexed ligand is in this finite area. The amount of ligand in the liquid sample is inversely proportional to the amount of label measured in the center of the finite area. Generally, label measurement is carried out after from about 5 to about 180 seconds after sample contact and spreading.

The following examples are provided to illustrate the practice of the present invention. In these examples, the materials used were obtained as follows:

rabbit anti-dilantin, anti-theophylline and anti-phenobarbital antisera from either Western Chemical Research Corp. (Fort Collins, Colo. U.S.A.) or Kallestad Laboratories, Inc. (Austin, Tex., U.S.A.), normal rabbit serum from Grand Island Biological Co. (Grand Island, N.Y. U.S.A.), or from Colorado Serum Co. (Denver, Colo. U.S.A.), glucose oxidase from Sigma Chemical Co. (St. Louis, Mo. U.S.A.), Zonyl TM FSN surfactant from DuPont (Wilmington, Del. U.S.A.), Peroxidase from Miles Laboratories (Napierville, Ill. U.S.A.), Alkanol TM XC surfactant from DuPont Co. (Wilmington, Del., U.S.A.), Brij TM 78 surfactant from ICI American, Inc. (Wilmington, Del., U.S.A.), Estane TM polyurethane resin from B. F. Goodrich (Cleveland, Ohio, U.S.A.), Triton TM X-405 surfactant from Rohm & Haas (Philadelphia, Pa., U.S.A.), and the remainder from Eastman Kodak Co. (Rochester, N.Y., U.S.A.), or prepared using known starting materials and procedures.

As used in the context of this disclosure and the claims, I.U. represents the International Unit for enzyme activity defined as one I.U. being the amount of enzyme activity required to catalyze the conversion of 1 µmole of substrate per minute under standard pH and temperature conditions for the enzyme.

EXAMPLE 1

Determination of Theophylline

An analytical element for the determination of theophylline was prepared having the following format and components:

| Spreading Layer | Polystyrene Beads (5–20 µm) coated with normal rabbit serum | 25–180 g/m² |
|---|---|---|
| | Poly(n-butyl acrylate-co-styrene-co-2-acrylamido-2-methylpropane sulfonic acid, sodium salt) [75:20:5 weight ratio] | 2–18 g/m² |

|   | | |
|---|---|---|
|   | adhesive | |
|   | Zonyl ™ FSN surfactant | 0.1–2.5 g/m² |
|   | S. aureus coated with | 2–20 g/m² |
|   | theophylline anti-serum | |
| Reagent | Gelatin (hardened) | 2–20 g/m² |
| Layer | Leuco Dye* | 0.025–0.6 g/m² |
|   | 2,4-di-n-Amylphenol | 0.9–3.6 g/m² |
|   | Dimedone | 0.05–0.5 g/m² |
|   | Alkanol ™ XC surfactant | 0.01–0.2 g/m² |
|   | Glucose | 0.9–6 g/m² |
|   | Peroxidase | 1,000–50,000 I.U./m² |
|   | Poly(ethylene terephthalate) | |
|   | Support | |

*4,5-bis(4-dimethylaminophenyl)-2-(4-hydroxy-3,5-dimethoxyphenyl)imidazole

A series of serum-based theophylline standards varying in concentration from 1 to 128 μg/ml was prepared. A 10 μl aliquot of each standard was mixed with a theophylline-glucose oxidase analog and diluent (0.01 molar potassium phosphate buffer, pH 7.0, containing 0.15 molar NaCl and 0.1% rabbit gamma globulin) such that the dilution of the standard was 1:40 and the concentration of the analog was $4 \times 10^{-8}$ molar. The resulting solutions were then spotted onto a finite area of the spreading layer of samples of the element using a single 10 μl drop of each solution. After incubation at 37° C. for 2–3 minutes after sample spotting, the reflection density was measured in the center of the finite area at 670 nm in a modified commercially available reflectometer. The Williams-Clapper transform (J. Optical Soc. Am., 43:595, 1953) was used to determine transmission density values. The results are listed in Table I below. As can be seen from the data, the rate of dye formation was inversely proportional to analyte concentration.

TABLE I

| Theophylline Concentration (μg/ml) | Rate $D_T$/minute |
|---|---|
| 1 | 0.157 |
| 2 | 0.145 |
| 4 | 0.131 |
| 8 | 0.110 |
| 16 | 0.085 |
| 32 | 0.082 |
| 64 | 0.068 |
| 128 | 0.061 |

EXAMPLE 2 and 3

Determination of Phenobarbital and Diphenylhydantoin (Dilantin)

Analytical elements containing the necessary reagents for the quantitative analysis of phenobarbital (Phe) and diphenylhydantoin (DPH) were prepared according to Example 1. The evaluation procedures in these examples were the same as the procedure described in that example, except that in the phenobarbital assay, the dilution factor was 1:75 and the phenobarbital-enzyme analog concentration was $3 \times 10^{-8}$ molar, and in the diphenylhydantoin assay, the dilution factor was 1:25 and the diphenylhydantoinenzyme analog concentration was $3 \times 10^{-8}$ molar. The assay results for phenobarbital are listed in Table II below. The assay results for diphenylhydantoin are listed in Table III below. In both examples, the rate of dye formation was inversely proportional to ligand concentration.

TABLE II

| Phe Concentration (μg/ml) | Rate $D_T$/minute |
|---|---|
| 0 | 0.161 |
| 1.4 | 0.154 |
| 2.6 | 0.142 |
| 5.2 | 0.136 |
| 10.4 | 0.116 |
| 20.8 | 0.107 |
| 41.3 | 0.093 |
| 80.8 | 0.081 |
| 165.0 | 0.069 |

TABLE III

| DPH Concentration (μg/ml) | Rate $D_T$/minute |
|---|---|
| 0.1 | 0.127 |
| 1.0 | 0.117 |
| 2.0 | 0.104 |
| 3.8 | 0.097 |
| 7.5 | 0.089 |
| 14.7 | 0.083 |
| 29.2 | 0.073 |
| 57.0 | 0.065 |
| 122.0 | 0.065 |

The invention has been described in detail with particular reference to preferred embodiments thereof, but it will be understood that variations and modifications can be effected within the spirit and scope of the invention.

We claim:

1. A method for the determination of an immunologically reactive ligand in a liquid using a dry analytical element, said element comprising a support having thereon a porous spreading layer which contains an immobilized receptor for an immunologically reactive ligand, said method consisting essentially of the steps of:

A. in the presence of a labeled ligand analog, contacting a finite area of said spreading layer with a sample of said liquid so as to form an immobilized ligand-receptor complex within said finite area and to effect substantially horizontal separation of uncomplexed ligand from said immobilized complex during liquid spreading, and B. at least about 5 seconds after the completion of said contacting, determining said immobilized complex within the center of said finite area.

2. The method of claim 1 wherein said immobilized complex is determined within an about 3 to about 5 mm diameter center of said finite area.

3. The method of claim 1 wherein step B is carried out within about 5 to about 180 seconds after the completion of said contacting step A.

4. The method of claim 1 wherein said liquid sample is applied to said element in a single sample volume over at least about 5 seconds.

5. The method of claim 1 wherein said liquid sample is applied to said element in two or more sequential sample volumes over at least about 5 seconds.

6. The method of claim 1 for the determination of a therapeutic drug.

7. The method of claim 6 for the determination of theophylline, phenobarbital or diphenylhydantoin.

8. The method of claim 1 wherein said ligand analog comprises an enzyme label and said element comprises an indicator composition in a reagent layer.

9. The method of claim 8 wherein said enzyme label is glucose oxidase, peroxidase or alkaline phosphatase.

10. The method of claim 1 wherein said spreading layer is composed of a particulate structure comprising a plurality of particles having a particle size of from about 1 to about 200 μm and being bonded to each other on surface areas of adjacent particles where said adjacent particles are in closest proximity to form a coherent, three dimensional lattice which is essentially nonswellable in an aqueous liquid.

11. The method of claim 10 wherein said Particles are chemically bonded to each other through reactive groups which are incorporated in said particles.

12. The method of claim 10 wherein said particles are bonded to each other with an adhesive material.

13. The method of claim 12 wherein said particles comprise an addition polymer formed from one or more of the following ethylenically unsaturated polymerizable monomers:
 (a) up to 100 weight percent of an aminosubstituent-free vinyl aromatic monomer,
 (b) up to about 25 weight percent of an acrylic acid ester,
 (c) up to 100 percent of a methacrylic acid ester,
 (d) up to about 30 weight percent of an ethylenically unsaturated carboxylic acid,
 (e) up to about 75 weight percent of an ethylenically unsaturated nitrile,
 (f) up to about 20 weight percent of an amino-substituted vinyl aromatic monomer,
 (g) up to about 20 weight percent of an ethylenically unsaturated monomer containing a crosslinkable group,
 (h) up to about 20 weight percent of a tertiary aminoalkyl acrylate or methacrylate,
 (i) up to 100 weight percent of an N-heterocyclic vinyl monomer, and
 (j) up to about 20 weight percent of an acrylamide or methacrylamide,
 and said adhesive comprises an addition polymer formed from a blend of ethylenically unsaturated polymerizable monomers selected from the following group:
 A. a blend containing from about 1 to about 35 weight percent of one or more amino-substituent-free vinyl aromatics and from about 65 to about 99 weight percent of one or more alkyl acrylates or methacrylates,
 B. a blend containing from about 20 to about 95 weight percent of one or more amino-substituent-free vinyl aromatics, acrylic or methacrylic acid esters or ethylenically unsaturated polymerizable monomers containing crosslinkable groups, and from about 5 to about 80 weight percent of one or more ethylenically unsaturated polymerizable monomers having an active hydrogen or salts thereof,
 C. a blend containing from about 15 to 100 weight percent of one or more ethylenically unsaturated monomers selected from the group consisting of 1-vinylimidazole, N-vinyl-2-pyrrolidone, vinylbenzyl alcohol, ethyl acrylate or an acrylamide or methacrylamide, and up to 85 weight percent of one or more ethylenically unsaturated polymerizable monomers containing crosslinkable groups, and
 D. a blend containing from about 60 to about 98 weight percent of one or more acrylic or methacrylic acid esters, and from about 2 to about 40 weight percent of one or more ethylenically unsaturated polymerizable monomers containing one or mole anionic moieties.

14. A method for the determination of an immunologically reactive ligand in a liquid using a dry analytical element, said element comprising a support having thereon a porous spreading layer containing an immobilized receptor for an immunologically reactive ligand, said layer being composed of a particulate structure comprising a plurality of particles having a particle size of from about 2 to about 20 μm and being bonded to each other on surface areas of adjacent particles where said adjacent particles are in closest proximity to form a coherent, three-dimensional lattice which is essentially nonswellable in an aqueous liquid, said method consisting essentially of the steps of:
 A. in the presence of a labelled ligand analog, contacting a finite area of said spreading layer with a sample of said liquid so as to form an immobilized ligand-receptor complex within said finite area, and to effect substantially horizontal separation of uncomplexed ligand from said immobilized complex during liquid spreading, and
 B. at least about 5 seconds after the completion of said contacting, determining said immobilized complex within the center of said finite area.

15. The method of claim 14 wherein said ligand analog comprises an enzyme label and said element comprises an indicator composition in a reagent layer.

16. The method of claim 14 wherein said ligand analog is incorporated into said element prior to contacting step A.

17. The method of claim 14 wherein said immobilized complex is determined within an about 3 to about 5 mm diameter center of said finite area, and
 said step B is carried out within about 5 to about 180 seconds after the completion of said contacting step A.

18. The method of claim 14 for the determination of theophylline, phenobarbital or diphenylhydantoin.

* * * * *